United States Patent
Cao

(10) Patent No.: US 6,660,305 B1
(45) Date of Patent: Dec. 9, 2003

(54) COMPOSITION FOR STIMULATING THE SYNTHESIS OF THE MELANIC PIGMENT AND PROCESS FOR OBTAINING IT

(75) Inventor: Carlos M. Miyares Cao, Habana (CU)

(73) Assignee: Centro de Histoterapia Placentaria (CU)

( * ) Notice: Subject to any disclaimer, the term of this patent is extended or adjusted under 35 U.S.C. 154(b) by 0 days.

(21) Appl. No.: 09/744,633

(22) PCT Filed: Jul. 28, 1999

(86) PCT No.: PCT/CU99/00003

§ 371 (c)(1),
(2), (4) Date: May 7, 2001

(87) PCT Pub. No.: WO00/06180

PCT Pub. Date: Feb. 10, 2000

(30) Foreign Application Priority Data

Jul. 28, 1998 (CU) .................................. 110/98

(51) Int. Cl.[7] .............................................. A61K 35/50
(52) U.S. Cl. ........................................................ 424/583
(58) Field of Search ................................ 424/583, 520, 424/59, 63; 514/21; 530/359, 851

(56) References Cited

U.S. PATENT DOCUMENTS 4,507,277 A * 3/1985 Cao et al.
5,690,966 A * 11/1997 Bhadra et al.
6,451,358 B2 * 9/2002 Zhao

OTHER PUBLICATIONS

Prajnamoy et al., Intl J of Dermatology (1995); 34(1): 61–66,. Hydroalcoholic human placental extract: Skin pigmenting activity and gross chemical composition.*

Schallreuter et al., Dermatology (1995); 190: 223–229. Treatment of vitiligo with a topical application of pseudocatalase and calcium in combination with short–term UVB exposure.*

Carsberg et al., J Dermatological Science (1995); 9:157–164. Intracellular calcium modulates the responses of human melanocytes to melanogenic stimuli.*

* cited by examiner

*Primary Examiner*—Christopher R. Tate
*Assistant Examiner*—Michele C. Flood
(74) *Attorney, Agent, or Firm*—Lackenbach Siegel LLP

(57) ABSTRACT

This invention relates to the field of human medicine, more specifically to dermatology, and in particular to a composition developed for the stimulation of the synthesis of the melanic pigment of the skin, therefore useful for the treatment of vitiligo. The technical goal of this invention is to provide a composition of natural origin useful in the treatment of vitiligo that has no toxic effects and no relapse. The composition obtained stimulates the synthesis of the melanic pigment of the skin and the reproduction of melanocytes, as demonstrated through pharmacological tests to which the composition was subjected, causing no serious secondary reactions at all, as demonstrated in the toxicological, teratological and clinical tests performed. The resulting product can easily be obtained and applied, repigmentation begins rapidly after initiating the treatment, and the effect is irreversible. The color acquired is identical to the color of the normal skin areas of the patient, but these areas do not further increase the intensity of their coloration after the product has been applied. The product can also be used for the treatment of any depigmentation process of the skin, for example, that caused by burns.

9 Claims, 1 Drawing Sheet

COMPOSITION FOR STIMULATING THE SYNTHESIS OF THE MELANIC PIGMENT AND PROCESS FOR OBTAINING IT

TECHNICAL SECTOR

This invention relates to the field of human medicine, more specifically to dermatology, and in particular to a composition developed for stimulating the synthesis of the melanic pigment of the skin, therefore useful in the treatment of vitiligo, as well as the procedure for obtaining that composition.

PRIOR ART

Vitiligo or leukoderma is one of the oldest known diseases of humanity, and is characterized by the loss of the cells that produce melanic pigment in the skin. This disease affects approximately 1% of the world's population, without distinction as to age, sex or race. It is of unknown etiology and no treatment has been found for it up to now. It appears as a gradual depigmentation of the skin of patients who are in situations of extreme nervous tension, and has an unfavorable affect on their psyche and social behavior as its external symptoms emerge, appearing as white areas of skin surrounded by a halo of hyperpigmentation, and manifesting themselves primarily on the face, trunk and around the joints.

Current technology recognizes that certain chemical substances of vegetable origin or produced semi-synthetically, known as psoralens, can be used in the treatment of vitiligo. These substances, administered orally or topically, concentrate in the melanocytes or cells that produce the dermic pigment, absorbing energy from ultraviolet radiation and stimulating the production of the pigment melanin. (Arnold, M. J. Jr. "Psoralens and Suntan," Hawaii Med. J., 1957–16391); (Becker, S. W. Jr. "Methods of Increasing Skin Pigmentation," J. Sec. Cosmetic Ehem., 1958-9-80); (Fitzpatrick, T.B. "Pigmentary Diseases," Current Therapy, 1958–314); (Becker, S. W. Jr. "Effects of 8-Methoxy Psoralen and Ultraviolet Light in Human Skin," Science, 1958-127-878); (Sidi, E. Planat, P. "Practical Considerations on Current Treatment of Vitiligo," Revue of Medicine, Dec. 23, 1968).

However, psoralens are not without toxic secondary effects, being capable of causing dermatitis and necrosis of the skin when applied topically. Furthermore, their effect is slow and reversible in the majority of cases when the medication is discontinued. In addition, these substances present some difficulties in application, which requires a gradually increasing daily period of ultraviolet radiation exposure for the patient, sometimes provoking severe toxic reactions such as burns resulting from their topical application, or hepatic insufficiency, digestive, renal and nervous disturbances from their oral administration.

The currently known technical solution that is most similar to this invention is Melagenina Lotion®, Patent FR 8220746. Melagenina Lotion® is a 50% human placenta alcoholic extract, which is obtained from healthy pregnant women under aseptic conditions after normal childbirth. This extract contains a lipoprotein with a molecular weight between 1500 and 4000 Daltons, which constitutes its active element. This substance stimulates the reproduction of the melanocytes and the synthesis of the melanic pigment, also accelerating the oxidation of the amino acid L-dopa in the presence of sunlight, which encourages its transformation into melanin after internal chemical processes.

Melagenina Lotion® has been used successfully for the treatment of vitiligo up to now. According to clinical trials that were performed, its use was noticeably effective among all the patients to whom it was applied. (Miyares Cao C., Taboas M. and López H. "Informe preliminar sobre el empleo de extracto placentario humano en la terapeutica del Vitiligo," [Preliminary Report on the Use of Human Placenta Extract in the Treatment of Vitiligo] Revista Cubana de Farmacia 10 (1). 1976; Miyares Cao C. et al. "Estudio experimental y clinico del efecto pigmentante epidermico del extracto placentario humano," [Experimental and Clinical Study of the Epidermal Pigmenting Effect of Human Placenta Extract] Revista Cubana de Farmacia, Volume 20, No. 6, November–December 1981; Sharma S. K.,. Jain R. K and Sharma A. K. "Topical Human Placental Extract for the Treatment of Vitiligo, A Preliminary Study"; Miyares C. et al., "Estudio experimental y clinico del efecto pigmentante epidermico del extracto placentario humano,"[Experimental and Clinical Study of the Epidermal Pigmenting Effect of Human Placenta Extract] Annais Brasileiros de Dermatologia, 1986: 61: 3 (Supplement); Miyares Cao C. "Melagenina Producto Cubano. Nuevo y Eficaz medicamento para el tratamiento del Vitiligo," [The Cuban Product Melaginina. A New and Effective Medication for the Treatment of Vitiligo] Serie de Resenas Nacionales, Ed. Palacio de las Convenciones. Havana, p. 15. 1986).

Melagenina Lotion®, although free of harmful side effects, is a product that must be used in three daily applications at 8-hour intervals and accompanied by sun or infrared exposure at one of the applications, which makes it difficult for many of the patients to complete the treatment.

Current technology also recognizes that calcium actively participates in the process of skin pigmentation, through the stimulation of the secreting action of the melanocytes in proportion to the concentration of this ion. (Meyer, A. 1986. "Influence of Calcium on the Melanocytes in the Inner Ear," Abst; 13th International Pigment Cell Conference Oct. 5–6, Tucson, Ariz., USA; and Negishi, S. 1986. "The Role of Calcium in Light Response of Onyzias Melonophores," Abst; 13th International Pigment Cell Conference Oct. 5–6, Tucson, Ariz., USA).

DISCLOSURE OF THE INVENTION

The new feature of the current invention consists of a new composition containing the same active ingredient as Melagenina Lotion®, in this case an alphalipoprotein obtained from human placental cotyledons by processing them with organic solvents and later redissolving them in a solution of ethanol with calcium chloride, making it possible to obtain a product that displays a synergic effect between the two components in their pigmenting effect, thus decreasing the number of applications of the product from 1 every 8 hours per patient, to 1 every 24 hours, also eliminating the need to expose the patient to solar or infrared radiation after any of the applications.

The new product thus obtained, referred to in this document as "Melagenina Plus," can be used in one single daily application, which is the current practice in therapy worldwide.

This product stimulates the synthesis of the melanic pigment of the skin and the reproduction of melanocytes, as demonstrated by the pharmacological trials that have been carried out, and completely lacks any severe secondary reactions, as shown by the toxicological, teratological and clinical trials performed. This product is easy to obtain and apply, and re-pigmenting begins quickly (15 to 20 days)

after beginning the treatment, being irreversible after discontinuing the application of the product. The color acquired by the skin where it is applied is identical to that of the normal areas of the patient's skin, which for their part do not increase the intensity of their coloring afterwards.

Because the raw material from which the active element of the product is extracted is a human tissue, there is no fear of immunological reaction, with no contraindications for its use for any age, sex or race.

Obtaining of the Active Principle of the Composition Melagenina Plus

The following procedure was performed to obtain the active element for the current invention:

A kilogram of placental cotyledons that had been left to freeze for 7 to 10 days was used. They were then ground and macerated in 90 to 96% ethanol in equal parts by weight/volume. The macerate was filtered through thick gauze and allowed to rest for 24 hours.

The pigmenting activity of the supernatant was measured, and was positive after 20 to 50 days of use in topical form on the ears of Balb/C 57 BL 6 mice.

10 ml of a saturated solution of benzoic acid in 90 to 96° ethanol, made by dissolving 2–8 g of benzoic acid in 5 to 12 ml of 90 to 96° ethanol, was added with a hypodermic needle to 200 ml of the extract containing the pigmenting factor.

The mixture was shaken for 10 to 50 minutes and filtered with No. 2 to 5 Whatman filter paper. Then the precipitate obtained was washed with 200 to 500 ml of a saturated solution of benzoic acid in distilled water, made by dissolving from 2 to 10 g of benzoic acid in 300 to 1000 ml of distilled water.

Afterwards, the precipitate was removed from the filter paper and added to 100 to 500 ml of 30% acetone, and centrifuged at 1500 rpm for 10 to 30 minutes, with the supernatant being discarded.

The precipitate was washed another 2 to 10 times with 100 to 500 ml of acetone, and vacuum dried at room temperature. The product was re-dissolved in 90 to 96° alcohol containing 0.2 to 4.0 mg/ml of calcium chloride.

Five ml of the above biologically active product was filtered through Sephadex G-30 or 100, using as a buffer sodium phosphate $5 \times 10-1$ to $5 \times 10-6$ moles, pH=4 to 8, which was packed in a column from 1 to 3 cm wide and from 18 to 40 cm high. The flow was from 10 to 30 drops per minute and the collected fractions were from 5 to 10 ml each.

Two proteic peaks were obtained, with the first one being 100 to 300 $\mu$g/ml and the second oneg 20 to 150 $\mu$g/ml. The pigmenting activity was positive for the second peak, appearing 10 to 20 days after the lyophilized mixture was topically used on the guinea pig.

The lyophilized mixtures of both proteic peaks were run in electrophoresis with polyacrylamide gel and in [agar]. The former was stained with a coloring for proteins (amido black) and the second was stained to detect lipids (Sudan dye). In the protein electrophoresis, a small, colored band followed by another without color was observed, both of them with little migration; a very visible band was also observed in the albumin region. In the lipids electrophoresis, a band was observed in the region where the alphalipoproteins migrate.

Synergic Pigmenting Effect of Melagenina and Calcium.

The melanocytopo[y]etic activity of the resulting product was evaluated by the once-daily topical application of Melagenina Plus for a period of 5 consecutive days on the epidermis of the ears of black mice of the B6 D2 strain. The trial used 60 black mice divided into 4 groups, named A, B, C and D, composed of 5 mice each, to which the following treatments were applied:

| Group | Daily Topical Treatment |
|---|---|
| A | 70% Alcohol, as vehicle for Melagenina ® (Control) |
| B | 70% Alcohol solution with the addition of calcium chloride in 1 mg/ml concentration |
| C | Melagenina Lotion ® |
| D | Melagenina Lotion ® with the addition to calcium chloride in 1 mg/ml concentration (Melagenina Plus) |

The 70% alcohol, the 70% alcohol solution with 1 mg/ml calcium chloride, and the Melagenina Lotion® and the Melagenina Plus were applied by being rubbed on the animals' ears by the operator's fingers.

When the treatment period was finished, 24 hours were allowed to elapse and the animals were killed in order to remove the epidermis of their ears and test them with the L-dopa oxidase histochemical method, which makes it possible to count, using a microscope, the melanocytes per $mm^2$ in this histological structure.

To determine the number of melanocytes per $mm^2$, 5 different areas were selected from the most densely populated zone of each ear, and using a special program developed for this purpose (specific section for counting of cells), the number of cells per $mm^2$ was determined for each of the 5 areas, so that 150-melanocyte-per-$mm^2$ values were obtained for each group (15 animals per group and 10 counts per animal).

The values obtained in the melanocyte-per-mm count were subjected to a simple classification-variance analysis and then to a Kruskal-Wallis test and a Student Newman-Keuls (SNK) test, in order to determine the groups between which there existed significant differences.

The results of this experiment can be seen in Table I, and are illustrated in FIG. 1.

TABLE I

Test of Kruskal-Wallis
Quantity of melanocytes/$mm^2$

| X | N | |
|---|---|---|
| 180.66 a | 150 | |
| 111.29 b | 150 | |
| 66.83 c | 150 | |
| 62.79[d] | 150 | for p < 0.001 | a = Melagenina Plus
b = Melagenina Lotion ®
c = 70% Alcohol + 1 mg/ml Calcium
d = 70% Alcohol It was found that for p<0.001, there was a significant increase in the number of melanocytes/$mm^2$ in the epidermis of the ears of the black mice treated with Melagenina Lotion® and Melagenina Plus, compared to the groups treated with alcohol and those not treated.

The increase in melanocytes was greater in the animals treated with Melagenina Plus.

Other differences found were:

There are significant differences between the results obtained using Melagenina Plus and using Melagenina Lotion® only.

There are significant differences between the results obtained using Melagenina Plus and using alcohol plus calcium only.

There are significant differences between the results obtained using Melagenina Plus and using alcohol only.

There are significant differences between the results obtained using Melagenina Lotion® and using alcohol plus calcium.

There are significant differences between the results obtained using Melagenina Lotion® and the control group that was treated with alcohol only.

There are no significant difference between the control group and the group treated with alcohol plus calcium.

In addition, it was demonstrated that when Melagenina Lotion® and Melagenina Plus are applied indiscriminately in biological trials, it was observed that, in the case of Melagenina Plus, the pigmenting effect is visible in the nipples of male guinea pigs in only 13 days, while this occurs in 18 days with Melagenina Lotion®. Similarly, a greater concentration of melanin is observed in the tails of the black mice using Melagenina Plus when the sections are treated by the histochemical method, where a greater increase in the melanocytes in the basal region of the epidermis is found.

Studies of Skin Irritation in Animals

The product Melagenina Plus was applied to a group of animals in a dose of 20 mg/cm2 on a 42 cm2 area and the solvent was applied to that same animal.

During the two weeks of the experiment no kind of irritation or effect on the skin was observed. The histopathological studies show no damage.

In conclusion, it can be stated that the product Melagenina Plus causes no irritation to the skin.

Clinical Trials in Humans

To perform these trials, 30 vitiligo patients were randomly selected.

The patients were separated by alternation into two groups, named I and II, and composed of 15 patients each.

Those belonging to group I were told to use Melagenina Lotion® (Alcoholic Extract of 50% Human Placenta], applying it topically by rubbing it with their fingers on the areas of skin depigmented by the illness, three times a day at 8-hour intervals (6:00 a.m., 2:00 p.m. and 10:00 p.m.).

On one of these occasions, the treated areas were to be exposed to 250-watt infrared lamps, placed at a distance of 40 cm, for 15 minutes. The application of the medication was to be repeated every 5 minutes during that time.

In turn, the members of Group II were to use Melagenina Plus (Alcoholic extract of 50% human placenta containing calcium chloride), applying it in a similar way but only once a day, without the exposure to infrared radiation and at 24-hour intervals.

The participants in the trial were to have remained without any specific treatment before beginning the trial.

The patients that were the subject of the experiment were evaluated monthly over a 6-month period established in order to compare the degree of repigmentation obtained with each product, as well as the appearance of secondary reactions, in the two groups.

Biopsies of the depigmented skin were performed at the beginning and end of the experiment in 5 randomly selected patients from each group.

The histological technique L-dopa Oxidase was used to identify the melanocytes in these patients.

At the same time, the difference in the consumption of bottles of the medication in each group was determined.

For statistical analysis of the percentage of reduction of depigmented body surface of each group, as well as for its determination for each patient, a program designed for this purpose was used (Coyula, R. "Automatizacion de la Creacion de Historia Clinica de los enfermos de Vitiligo. 1ra Conferencia Latinoamericana de Aplicaciones de la Matematica y la Computacion a la Biologia." [Automation of the Creation of Clinical History of Vitiligo Patients. 1st Latin American Conference on the Application of Mathematics and Computing to Biology] CENIC, Oct. 31–30 Nov. 30, 1991, Havana, Cuba).

The results obtained in this clinical trial are summarized in Tables II, III, IV and V, using as patient data their medical-record number as identification, and their age, sex, race and the years they have suffered from the disease. Among the parameters evaluated are the % of depigmentation at the beginning and the end of the treatment, the % of pigmentation obtained and the bottles of the medication consumed during this treatment. In addition, the analysis of the areas treated for each of the patients (face, neck, trunk, extremities or genitals) is shown in the table pertaining to each treatment type.

TABLE II

Results obtained using Melagenina Lotion ®

| PATIENT REC. NO. | AGE (YEARS) | SEX | RACE | YEARS OF ILLNESS | % DEPIGM. BEGIN | % DEPIGM. END | % PIGM. | BOTTLES |
|---|---|---|---|---|---|---|---|---|
| 255 | 13 | M | B | 12 | 26 | 16 | 10 | 18 |
| 268 | 14 | F | W | 3 | 8 | 3 | 5 | 6 |
| 277 | 12 | F | W | 2 | 5 | 2 | 3 | 6 |
| 286 | 5 | F | W | 2.6 | 6 | 0 | 6 | 6 |
| 292 | 10 | F | W | 3 | 24 | 21 | 3 | 18 |
| 293 | 56 | F | W | 12 | 11 | 9 | 2 | 12 |
| 381 | 34 | F | W | 10 | 23 | 16 | 7 | 18 |
| 591 | 21 | F | M | 11 | 59 | 39 | 20 | 98 |
| 674 | 5 | M | M | 3 | 58 | 30 | 28 | 48 |
| 771 | 4 | M | W | 0.2 | 8 | 5 | 3 | 6 |
| 849 | 44 | F | B | 10 | 13 | 8 | 7 | 12 |

TABLE II-continued

Results obtained using Melagenina Lotion ®

| PATIENT REC. NO. | AGE (YEARS) | SEX | RACE | YEARS OF ILLNESS | % DEPIGM. BEGIN | % DEPIGM. END | % PIGM. | BOTTLES |
|---|---|---|---|---|---|---|---|---|
| 838 | 5 | F | W | 0.6 | 8 | 2 | 6 | 6 |
| 852 | 5 | M | B | 3.5 | 43 | 32 | 11 | 48 |
| 1021 | 12 | F | M | 3 | 8 | 4 | 4 | 6 |
| 1044 | 27 | M | W | 5 | 9 | 3 | 6 | 6 |

TABLE III

Areas analyzed in patients treated with Melagenina Lotion ®
AREAS AFFECTED BY VITILIGO

| PATIENT REC. NO. | FACE | NECK | TRUNK FRONT | TRUNK BACK | EXTREMITIES SUP. | EXTREMITIES INF. | GENITALS |
|---|---|---|---|---|---|---|---|
| 255 | | | X | | X | | X |
| 268 | X | | | | | | |
| 277 | X | | X | | X | | |
| 286 | | | X | X | | | |
| 292 | X | | | | | X | |
| 293 | X | | | | X | X | |
| 381 | X | | X | | X | X | X |
| 591 | | X | X | | X | X | |
| 674 | | | | X | X | X | |
| 771 | | | X | X | | X | |
| 849 | | | X | X | | X | |
| 838 | X | | | | | X | |
| 852 | X | | X | | X | X | |
| 1021 | X | | | | | X | |
| 1044 | | | | | X | X | |

TABLE IV

Results obtained using Melagenina Plus

| PATIENT REC. NO. | AGE (YEARS) | SEX | RACE | YEARS OF ILLNESS | % DEP. BEGIN | % DEP. END | % PIGM. | BOTTLES |
|---|---|---|---|---|---|---|---|---|
| 2 | 20 | M | M | 1 | 2 | 0.5 | 1.5 | 1 |
| 31 | 1 | F | W | 5 | 6 | 2 | 4 | 2 |
| 126 | 5 | F | B | 0.2 | 1 | 0.5 | 0.5 | 1 |
| 154 | 9 | F | W | 0.5 | 39 | 7 | 22 | 8 |
| 219 | 3 | F | W | 8 | 40 | 7 | 13 | 8 |
| 231 | 8 | F | W | 9 | 11 | 3 | 8 | 4 |
| 341 | 3 | M | W | 1 | 4 | 2 | 2 | 2 |
| 486 | 5 | F | B | 2 | 4 | 1 | 3 | 2 |
| 491 | 5 | F | M | 4 | 24 | 1 | 3 | 6 |
| 733 | 5 | F | W | 3 | 13 | 0 | 3 | 4 |
| 779 | 3 | F | B | 0.6 | 4 | 2 | 2 | 2 |
| 781 | 3 | M | W | 23 | 6 | 3 | 3 | 2 |
| 888 | 7 | M | W | 0.2 | 12 | 6 | 6 | 4 |
| 1096 | 6 | F | W | 14 | 14 | 0 | 4 | 4 |
| 1116 | 4 | M | W | 1 | 22 | 2 | 10 | 6 |

TABLE V

Areas analyzed in patients treated with Melagenina Plus
AREAS AFFECTED BY VITILIGO

| PATIENT REC. NO. | FACE | NECK | TRUNK BEGIN | TRUNK END | EXTREMITIES SUP. | EXTREMITIES INF. | GENITALS |
|---|---|---|---|---|---|---|---|
| 2 | X | | | | | | |
| 31 | | | | | X | X | |
| 126 | | | | | | | X |
| 154 | X | | X | | X | X | X |
| 219 | X | | X | X | X | X | |
| 231 | X | | | | X | X | X |
| 341 | | | | | | X | |
| 486 | | | | | X | | |
| 491 | X | | X | | X | X | |
| 733 | | | X | | | X | |
| 779 | | | | X | X | | |
| 781 | | | | | | X | X |
| 888 | X | | | X | | | |
| 1096 | X | X | | | X | | X |
| 1116 | | | | | X | | X |

On the basis of the preceding tables, it can be observed that at the conclusion of 6 months of treatment, an average value of 59.11% in the reduction of body surface depigmented by the disease can be seen in the group treated with Melagenina Lotion®, and 50.79% in that treated with Melagenina Plus, without any significant difference being found between the two results, for a value p<0.05.

No local or systemic secondary reactions were recorded in the patients of the trial groups.

The biopsies performed on the 5 patients from each group showed the reappearance of melanocytes in the vitiligo areas selected for the pre- and post treatment histological study.

Finally, greater consumption of bottles of medication was observed in the group treated with Melagenina Lotion®, with a total of 264 and an average of 17.6 bottles per patient for the 6 months of the experiment, while the group treated with Melagenina Plus alone used only 56 bottles, with an average of 3.7 bottles per patient in the same time period. The histological study carried out demonstrated that the repigmenting effect of both products on the areas affected by vitiligo results from the fact that they both induce the reproduction of melanocytes in those areas.

The absence of systematic, local secondary reactions reaffirms that both products are harmless.

The synergic action of calcium and Melagenina facilitates compliance on the part of vitiligo patients, reducing the number of daily applications of the product and, as a result, the consumption of bottles for each treatment. In addition, the new formula makes it possible to eliminate the need for exposing the patient to solar or infrared radiation after the application.

Figure 1:
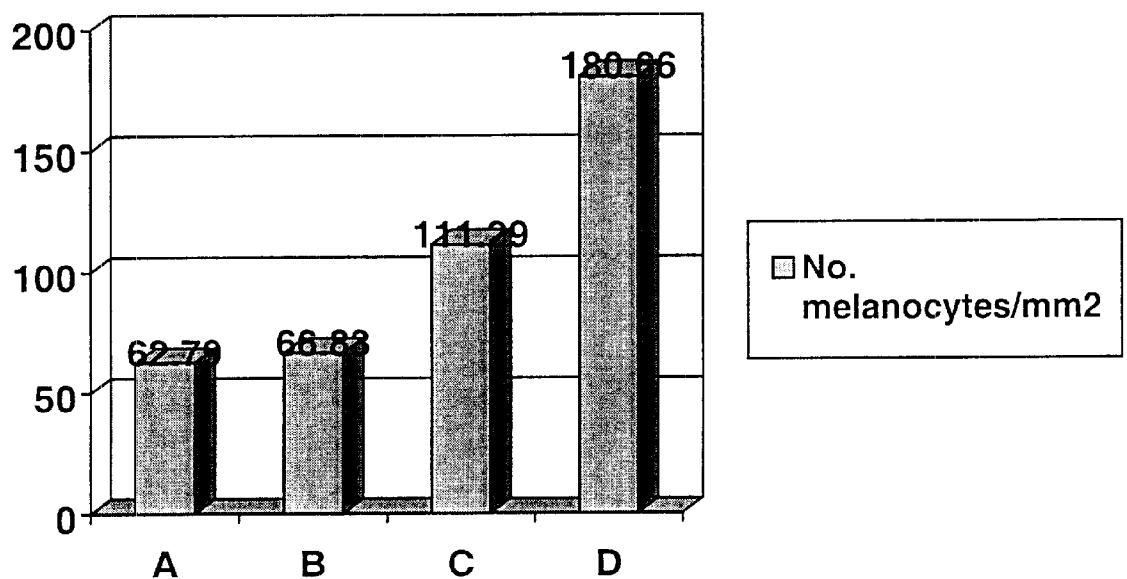
FIG. 1 shows the melanocytopo[y]etic action obtained through testing on the ears of black mice in 4 groups named A, B, C and D, to which the following treatments were applied.

A=melagenina plus
b=melagenina lotion®
c=70% alcohol solution +1 mg/ml calcium
d=70% alcohol solution

What is claimed is:

1. A method for the treatment of vitiligo in a mammal in need thereof comprising the step of:
   topically applying to an affected skin area of said mammal a mixture comprising;
   (i) alcohol,
   (i) an extract of human placenta in a weight that is about 50% of the weight of said alcohol, and
   (ii) calcium chloride in an amount between 0.2 and 4.0 mg per mL of said alcohol.

2. The method of claim 1, wherein the step of topically applying the mixture to an affected skin area is repeated once a day for a period of time between six months and one year.

3. The method of claim 1, wherein the affected skin area is not exposed to solar or infrared radiation when the mixture is on the affected area of the skin.

4. A composition for stimulating the synthesis of a mammalian's melanic pigment, comprising:
   alcohol,
   an extract of human placenta in a weight that is about 50% of the weight of said alcohol, and calcium chloride in an amount between 0.2 and 4.0 mg per mL of said alcohol.

5. The method of claim 1, wherein the alcohol is ethanol having a concentration of about 90% to about 96% by volume.

6. The composition of claim 4, wherein the alcohol is ethanol having a concentration of about 90% to about 96% by volume.

7. A method for stimulating the synthesis of melanic pigment in a mammal in need thereof comprising the step of:
   topically applying to an affected skin area of said mammal a mixture comprising:
   (i) alcohol,
   (i) an extract of human placenta in a weight that is about 50% of the weight of said alcohol, and
   (ii) calcium chloride In an amount between 0.2 and 4.0 mg per mL of said alcohol.

8. The method of claim 7, wherein the step of topically applying the mixture to an affected skin area is repeated once a day for a period of time between six months and one year.

9. The method of claim 7, wherein the affected skin area is not exposed to solar or infrared radiation when the mixture is on the affected area of the skin.

* * * * *